(12) United States Patent
Ollivier

(10) Patent No.: US 9,884,185 B2
(45) Date of Patent: *Feb. 6, 2018

(54) INTRACARDIAC CAPSULE IMPLANTABLE ON A THIN WALL, INCLUDING THE SEPTUM WALL

(71) Applicant: SORIN CRM SAS, Clamart (FR)

(72) Inventor: Jean-François Ollivier, VIlliers-le-Bâcle (FR)

(73) Assignee: SORIN CRM SAS, Clamart (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/374,701

(22) Filed: Dec. 9, 2016

(65) Prior Publication Data

US 2017/0157391 A1   Jun. 8, 2017

Related U.S. Application Data

(63) Continuation of application No. 14/559,796, filed on Dec. 3, 2014, now Pat. No. 9,517,337.

(30) Foreign Application Priority Data

Dec. 4, 2013   (FR) ..................................... 13 62125

(51) Int. Cl.
*A61N 1/05* (2006.01)
*A61N 1/372* (2006.01)
*A61N 1/375* (2006.01)

(52) U.S. Cl.
CPC ......... *A61N 1/0573* (2013.01); *A61N 1/3756* (2013.01); *A61N 1/37205* (2013.01)

(58) Field of Classification Search
CPC .... A61N 1/059; A61N 1/0573; A61N 1/3756; A61N 1/37205

(Continued)

(56) References Cited

U.S. PATENT DOCUMENTS 6,409,674 B1   6/2002   Brockway et al.
9,517,337 B2*  12/2016  Ollivier .................. A61N 1/059

(Continued)

FOREIGN PATENT DOCUMENTS

EP   2 394 695 A1   12/2011
EP   2 537 555      12/2012

OTHER PUBLICATIONS

Foreign Search Report for French Patent Application No. FR 1362125, dated Apr. 17, 2014, 2 pages.

*Primary Examiner* — Carl H Layno
*Assistant Examiner* — Jon Eric C Morales
(74) *Attorney, Agent, or Firm* — Foley & Lardner LLP

(57) ABSTRACT

An intracardiac capsule comprises a cylindrical body having an atraumatic rounded surface and a helical anchoring screw integral with the cylindrical body. The helical anchoring screw is able to penetrate tissue of a wall of the heart and is configured to provide temporary attachment, in rotation and in translation, of the capsule to an implantation site. The helical anchoring screw surrounds at least a portion of the length of the cylindrical body forming a contact region intended to come into contact with the wall of the cavity of the heart. Over the length of the contact region, the external diameter of the cylindrical body is less than the inner diameter of the helical anchoring screw, so as to leave a free gap there between. The helical anchoring screw is secured to the cylindrical body near the proximal end of the contact region, and extends freely to the opposite distal end.

20 Claims, 2 Drawing Sheets

(58) Field of Classification Search
USPC .......................................................... 607/127
See application file for complete search history.

(56) References Cited

U.S. PATENT DOCUMENTS

| | | |
|---|---|---|
| 2007/0088397 A1 | 4/2007 | Jacobson |
| 2008/0109054 A1 | 5/2008 | Hastings et al. |
| 2009/0082827 A1 | 3/2009 | Kveen et al. |
| 2011/0307043 A1 | 12/2011 | Ollivier |
| 2012/0095539 A1 | 4/2012 | Khairkhahan et al. |
| 2013/0268042 A1 | 10/2013 | Hastings et al. |

* cited by examiner

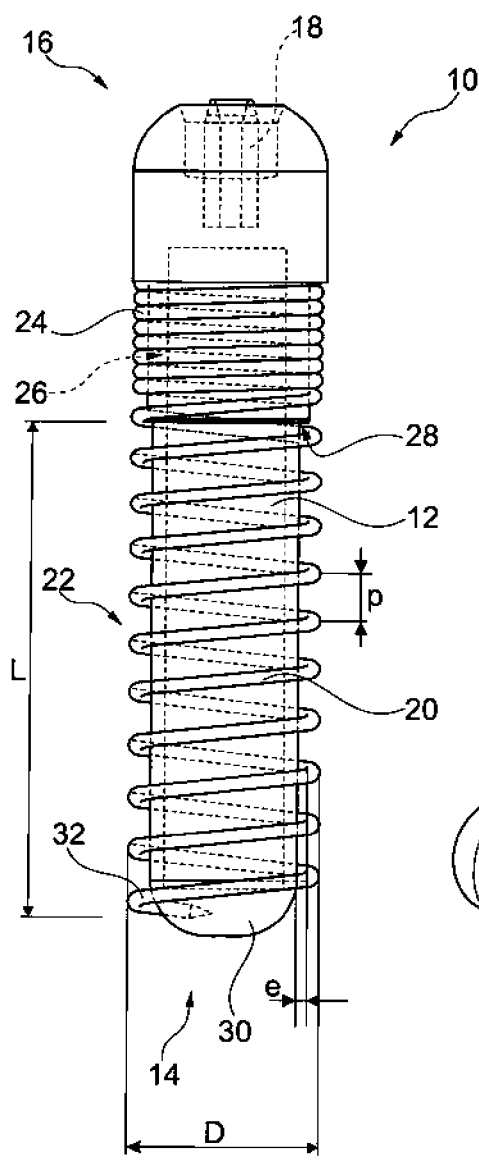
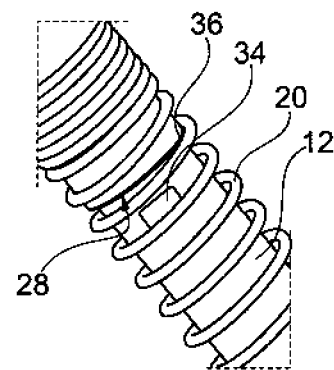
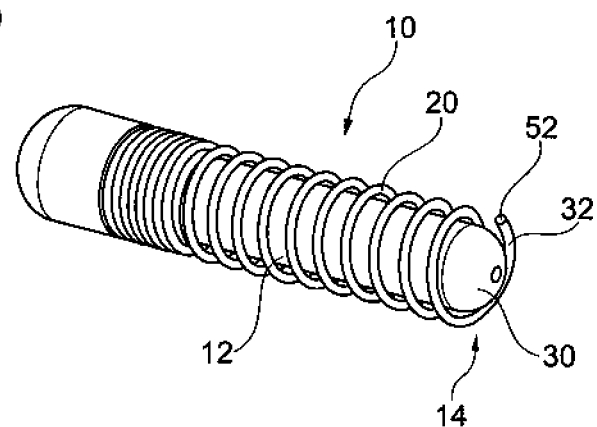
Fig. 1
Fig. 2
Fig. 3

INTRACARDIAC CAPSULE IMPLANTABLE ON A THIN WALL, INCLUDING THE SEPTUM WALL

CROSS REFERENCE TO RELATED APPLICATIONS

This application is a continuation of U.S. application Ser. No. 14/559,796, is now U.S. Pat. No. 9,517,337, filed Dec. 3, 2014, which claims the benefit of and priority to French Patent Application No. 1362125, filed Dec. 4, 2013, both of which are hereby incorporated by reference herein in their entireties.

BACKGROUND

The invention relates to "active implantable medical devices" as defined by Directive 90/385/EEC of 20 Jun. 1990 of the Council of the European Communities, specifically implants to continuously monitor heart rhythm and deliver to the heart, if necessary, electrical pulses for stimulation, resynchronization and/or defibrillation in case of rhythm disorder detected by the device.

The invention relates more particularly to devices in the form of an autonomous capsule implantable in a heart chamber (ventricle, atrium or even the arterial left heart chamber), hereinafter referred to as "autonomous capsule" or "leadless capsule." These capsules are devoid of any physical connection to a main implantable device (such as the housing of a pacing pulse generator) or non-implantable device (external device such as a programmer or a monitoring device for remote monitoring of the patient). They are referred to as leadless capsules therefore, to distinguish them from the sensors or electrodes located at the distal end of a conventional probe (lead), covered along its length by one or more conductors galvanically connecting the electrode or the sensor to a generator which is connected to an opposite proximal end to the lead.

However, as will be understood from the description herein, the autonomous nature of the capsule is not inherently a necessary feature of the invention, and that the latter can be applied to capsules permanently mounted at the distal end of a lead.

To hold the leadless capsules in place after implantation, they are provided with an anchoring element, usually having a projecting helical screw extending axially of the capsule body and adapted to penetrate the heart tissue at the implantation site by screwing, according to a similar method as for conventional screw leads.

EP 2394695 A1 (Sorin CRM SAS) describes such a type of screw leadless capsule and its accessory for the implantation at the selected site by docking of the axial screw and rotary drive of the capsule to secure it to the heart wall, wherein it will be maintained by the anchoring axial screw. Similar systems have been proposed implementing needles, hooks, barbs, etc., these anchoring members extending the capsule at its distal end so as to penetrate the tissue and anchoring the capsule from this end.

Regarding the capsule itself, it is generally cylindrical with a length between 20 to 40 mm in the case of leadless capsules, this cylindrical form being dictated by the access route via the peripheral venous system.

The configuration as described above (cylindrical body and axial anchorage) is compatible with implantation in the region of the apex, at the base of the ventricle, but can cause a number of problems for other implantation sites, for example on the ventricular or the atrial septum. Indeed, the small width of the right ventricular cavity, combined with the heartbeat, may cause deleterious repeated contact of the proximal portion of the capsule with the free wall of the heart muscle, the tricuspid valve or the pillars. Moreover, the area of the apex is not always the best target site for certain therapies, and may pose a risk because of the thinness of the wall in adjacent areas, creating a significant risk of perforation by the anchoring member during the implantation operation.

A further difficulty is that the implantation accessory (as described in the aforementioned EP 2394695 A1) generally places the capsule with its main axis in the extension of a catheter or of a stylet of the accessory, so as to go through the peripheral venous system and direct the capsule to the implantation site. For directing the capsule towards the apex of the ventricle, such an accessory is very suitable and can accurately be delivered and fully secured to the selected implantation site. Then the capsule can be anchored and then disconnected from the implantation accessory.

However, if it is desired to implant the capsule for example on the septal wall or on the right atrium wall, in order to anchor the screw it is necessary to perpendicularly access this wall with the capsule. This involves having a system with an adjustable head, especially complicated to handle with the heart beat because the head capsule is not naturally directed to the site of implantation, because of the elongate tubular shape of the capsule. To reduce this risk, flattened capsules have been proposed, for example EP 2537555 A1 (Sorin CRM SAS), the implementation of which is, however, more complex than that of tubular elongated capsules because their shape is not naturally suited for the passage in a vessel.

Various exemplary embodiments as disclosed herein propose an elongate tubular capsule, notably of the leadless type, specifically adapted for implantation on the interventricular septum or any other wall, including the thin or thick walls of the different heart chambers.

SUMMARY

Essentially, the capsule of the invention includes a tubular body combined with an anchoring helical screw. But instead of having the screw axially positioned in the extension of the capsule to the distal end thereof, this screw is wound around the tubular body, along at least a portion of the length of the tubular body. In its final configuration, the capsule is thus found contiguous to the target wall, that is to say that the axis of the tubular body of the capsule will be substantially parallel to the wall, instead of being introduced approximately perpendicularly thereto as in the case of conventional capsules with a projecting axial screw. The capsule according to the invention is maintained against the wall by wedging the tissues between the turns of the screw and the body of the capsule, along a generatrix of the latter.

According to U.S. 2013/0268042 A1 and U.S. Pat. No. 6,409,674 B1, there are capsules equipped with an anchoring screw with a large diameter which is partially wrapped around the body of the capsule. However, these capsules are intended to be anchored perpendicularly (not in parallel) to the wall, according to the conventional configuration of implantation. The capsule is provided for this purpose on its distal end with a tip, a harpoon and/or barbs to penetrate that end of the body in the wall and to keep it there in place. The screw portion wound around the body then has a secondary role, to enhance the holding in place of the body part which is embedded into the wall.

Specifically, the invention discloses an intracardiac capsule including: a cylindrical body; an anchoring helical screw secured to the cylindrical body, suitable for penetrating a tissue of a wall of a cavity of the heart; and, at a proximal end of the cylindrical body, methods for temporarily securing in rotation and in translation, the capsule to an implantation accessory.

The helical anchoring screw surrounds the cylindrical body on at least a part of the length thereof, this part forming a contact region adapted to come in contact with the wall of the cavity of the heart. On the extent of the contact region, the external diameter of the cylindrical body is less than the inner diameter of the helical anchoring screw, so as to leave a free space between the cylindrical body and the helical anchoring screw. The helical screw is secured to the cylindrical body in the vicinity of the proximal end of the contact region, and extends freely from this proximal end to the opposite distal end.

According to exemplary embodiments of the invention, said contact region extends along a generatrix of the cylindrical body and the distal end of the cylindrical body includes an atraumatic rounded surface.

In one exemplary embodiment, an intracardiac capsule includes a cylindrical body having an atraumatic rounded surface and a helical anchoring screw integral with the cylindrical body. The helical anchoring screw is able to penetrate tissue of a wall of a cavity of the heart and is configured to provide temporary attachment, in rotation and in translation, of the capsule to an implantation site. The helical anchoring screw surrounds at least a portion of the length of the cylindrical body forming a contact region intended to come into contact with the wall of the cavity of the heart. Over the length of the contact region, the external diameter of the cylindrical body is less than the inner diameter of the helical anchoring screw, so as to leave a free gap between the cylindrical body and the helical anchoring screw. The helical anchoring screw is secured to the cylindrical body in the vicinity of the proximal end of the contact region, and extends freely from the proximal end to the opposite distal end. The contact region extends along a generatrix of the cylindrical body.

In another exemplary embodiment, a method of implanting an intracardiac capsule includes positioning an intracardiac capsule against a tissue wall at an implantation site, such that an axis of the capsule forms an acute angle relative to the tissue wall. The intracardiac capsule including a cylindrical body and a helical anchoring screw integral with the cylindrical body. The helical anchoring screw is able to penetrate the tissue wall and is configured to provide temporary attachment, in rotation and in translation, of the capsule to the implantation site. The helical anchoring screw surrounds at least a portion of the length of the cylindrical body forming a contact region intended to come into contact with the tissue wall. Over the length of the contact region, the external diameter of the cylindrical body is less than the inner diameter of the helical anchoring screw, so as to leave a gap between the cylindrical body and the helical anchoring screw. The helical anchoring screw is secured to the cylindrical body in the vicinity of the proximal end of the contact region, and extends freely from the proximal end to the opposite distal end. The method further includes imparting a rotational movement on the capsule to cause progression of the helical anchoring screw in the tissue wall. The method further includes, as the helical anchoring screw progresses into the tissue wall in rotation and in translation, causing a portion of the tissue wall to be received in the gap between the helical anchoring screw and the cylindrical body, thereby securing the capsule to the tissue wall In yet another exemplary embodiment, an intracardiac capsule comprises a cylindrical body and a helical anchoring screw surrounding at least a portion of the length of the cylindrical body. The helical anchoring has a proximal end coupled to the cylindrical body and a free distal end able to penetrate tissue of a wall of a cavity of the heart. A gap is provided along at least a portion of the length of the cylindrical body between the helical anchoring screw and the cylindrical body to receive tissue of the wall of the cavity of the heart therein when the anchoring screw penetrates the tissue.

Accordingly to some embodiments, the capsule includes various advantageous subsidiary characteristics. In some embodiments, the anchoring screw does not extend beyond the end of the atraumatic rounded surface in the axial direction or, on the contrary, extends beyond this end to the extent of one or two screw turns. In some embodiments, the atraumatic rounded surface is shaped as to leave exposed the end of the anchoring screw over a length of one or two front turns, so as to provide a greater space between the anchoring screw and the capsule body, making the end of the anchoring screw more accessible for engagement of the screw in the wall of the cavity of the heart by these exposed turns. In some embodiments, the free gap remaining between the cylindrical body and the helical anchoring screw along the contact region is between 0.1 and 1 mm. In some embodiments, the cylindrical body further includes in the vicinity of the proximal end of the contact region an abutting shoulder whose diameter is greater than that of the contact region, the free span extending distally from this abutting shoulder. In some embodiments, the capsule further includes at least one section detection/stimulation electrode disposed on the cylindrical body, preferably near the abutting shoulder. In some embodiments, the helical anchoring screw is a screw made of an electrically conductive material covered with an electrically insulating coating with the exception of at least one area locally exposed forming a detection/stimulation electrode. In some embodiments, the free interval is a constant interval along the length of the contact region, or a variable interval along the length of the contact region, this interval being increased proximally. And, in some embodiments, the screw thread of the helical anchoring screw has a constant value, or is variable, this thread being reduced at the proximal side.

DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements and in which:

FIG. 1 is a view in elevation of a capsule according to the invention.

FIG. 2 is a detail of the central portion of the capsule, showing the configuration of a stimulation electrode.

FIG. 3 is a perspective view of the capsule of the invention, ready for implantation.

DETAILED DESCRIPTION

Figure 4:
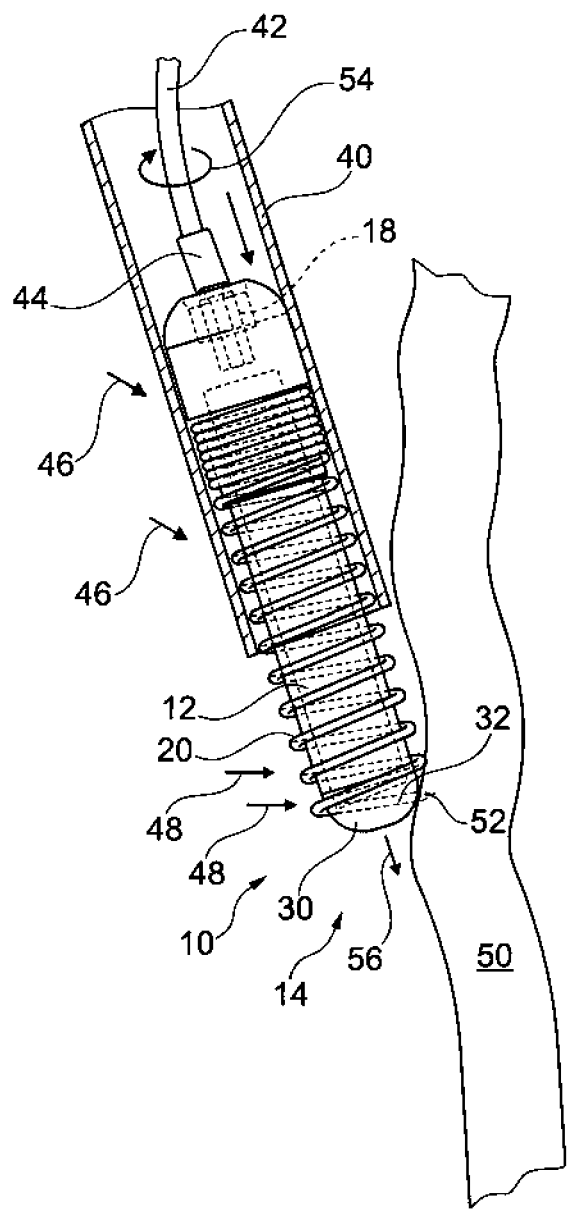
FIG. 4 is a view showing the initial approach phase of the capsule against the heart wall during the implantation operation, with the end of the implantation accessory.

An example of realization of the invention will now be described. In the figures, the reference 10 generally designates a leadless capsule, which is in the form of an elongate tubular member including a cylindrical body 12 with a distal portion 14 and a proximal portion 16.

The proximal portion 16 carries a temporary attachment mechanism, to attach the capsule to an implantation accessory in translation and in rotation (not shown in this figure). The attachment mechanism 18 may for example include an axial smooth rod on which a disengageable mechanism connected to a stylet or in a catheter is hafted for driving the capsule in rotation. Such a simple disengageable mechanism is described for example in the French patent application FR 1356020 filed on Jun. 24, 2013, on behalf of Sorin CRM SAS, for an "intracardiac capsule and in situ implantation accessory site via the femoral artery." Basically, this mechanism consists of a helical spring used in radial compression, for the pinch effect and not for its axial tension/compression effect. Such a spring plays both the role of a disengageable connection mechanism and of a torque limiter against an excessive screwing action that could lead to a "core" of tissue.

The capsule 10 also includes a helical anchoring screw 20 which, in a manner characteristic of the invention, is wound around the cylindrical body 12 on a portion of the length of the capsule, referred to as "contact region" 22. On the proximal side, the screw is secured to the tubular body 12, e.g. by clamping the most proximal turns 24 on a region 26 of the tubular body, proximally extending from the contact region 22. The region 26 has an increased diameter compared to the contact region 22, so as to form a stop shoulder 28 defining the proximal limit of the contact region 22.

The helical anchoring screw 20 is free along the extent of the contact region 22, to the distal end 14 of the cylindrical body. This distal end 14 includes an atraumatic rounded surface 30. In the example shown, the screw 20 does not extend beyond the end of the surface 30 in the axial direction, but other screw geometries can be envisaged, in particular with one or two turns extending from the rounded surface 30. The rounded shape of the surface 30, however, allows to leave exposed the end 32 of the screw 20, over a length of the order of one or two front turns (as shown in FIG. 3), so as to provide a greater space between the anchoring screw 20 and the capsule body 12, making the end 32 of the anchoring screw 20 more accessible for initiating the screwing in tissues exposed by these exposed turns, as will be described later.

The overall diameter D of the capsule, corresponding to the outer diameter of the helical anchoring screw 20, is preferably of the order of D=6 mm. The screw 20 is made of a material such as stainless steel, platinum-iridium alloy or another biocompatible material, in the form of a wire of a diameter typically from 0.3 to 0.8 mm spirally wound with a pitch p from 0.8 to 4 mm (these dimensions are in no way limiting and merely given as an example). The screw 20 extends over a contact region the length L of which may represent 20-80% of the total length of the capsule 10.

According to an exemplary embodiment, the inner diameter of the helical anchoring screw 20 is greater than the outer diameter of the cylindrical body 12 so as to leave a free gap e typically of the order of e=0.1 to 1 mm over the entire the length of the contact region 22.

The cylindrical body 12 carries, in the illustrated example, a segment electrode 34 (FIG. 2). Indeed, in order to preserve the pacing performance, it is desirable to limit the surface of the electrode, which can be done by limiting the opening angle thereof ("segment electrode"). To ensure a proper orientation during implantation for this segment electrode with respect to the tissue, the angular position of the screw 20 relative to the capsule is adjusted so that the center of the electrode 34 lies in close proximity to the last turn, which ends at the intersection 36 of the screw path and of the abutment shoulder 28, preferably within a sector of 120° upstream from the end of the thread generatrix. This ensures the physical contact of the segment electrode 34 with the tissues against which the capsule will be implanted, and thus preserves the electrical performance of the capsule.

Alternatively or in addition to a segment electrode, it is possible to form an electrode directly on the helical anchoring screw 20, the latter then being made of a conductive material covered with an electrically insulating coating, except one or more areas wherein the insulating coating has been locally ablated so as to expose the conductive material of the screw, which in contact with the tissues, form one or more detection/stimulation electrodes.

The implantation operation of a capsule 10 according to the invention just described above will now be made with reference to FIGS. 4 and 5. It is possible to use for the implantation a guiding and maneuver accessory like that of the French application FR 1356020 cited above, which is hereby incorporated by reference in its entirety and which describes an implantation accessory implementing a remotely adjustable catheter distally extended by a protective cylindrical tip 40 containing the capsule to be implanted.

The capsule is initially held in a retracted position in the tip, with the capsule connected to a stylet or to a sub-catheter 42 inserted into the inner lumen of the implantation accessory, the capsule 10 and the sub-catheter 42 being temporarily linked by a releasable mechanism 44 for securing in rotation and in translation these two elements, in particular to allow a complete screwing of the capsule in the tissue.

The telescopic configuration of the sub-catheter assembly 42/capsule 10 relative to the tip 40 can be projected out of the capsule out of this tip and beyond it over several centimeters, permitting in all circumstances a comprehensive and accurate approach of the capsule to the implantation site.

The tip 40 is operated so as to push it against the septum (for implantation on this site) and the capsule is then exited from the tip 40, the tip-capsule assembly being plated (arrows 46) against the wall so that the axis of the capsule forms an acute angle with the surface of the wall.

This operation maintains a tangential force (arrow 48) against the wall and thus ensures the anchoring of the end 52 of the first turn 32 of the screw in the tissue 50. The further rotational movement imparted to the capsule by the sub-catheter 42 (arrow 54) then generates a progression of the screw 50 into the tissue (arrow 56) thereof being wedged between the turns of the screw and the body of the capsule on a generatrix thereof.

The process continues until the tissue 50 abuts against the shoulder 28 (configuration illustrated FIG. 5) formed on the body of the capsule. This stop will cause an abrupt increase in the reaction torque on the sub-catheter 42, which will cause disengagement of the temporary fastening mechanism 44, while protecting the tissue from being torn.

Figure 5:
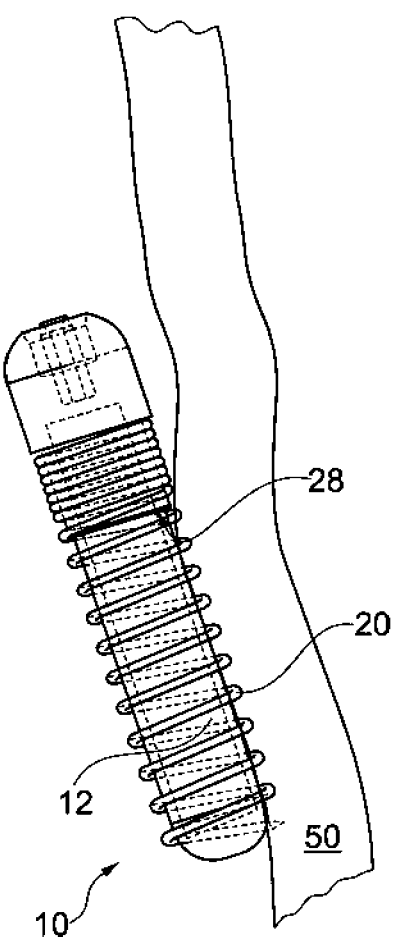
FIG. 5 is the counterpart of FIG. 4, showing the capsule in its final implanted position, after removal of the implantation accessory.

The final configuration is shown FIG. 5. As can be seen, the capsule is particularly well attached to the wall 50, due to the large number of turns insuring this securing. Also, the penetration being, by design, very superficial, the perforation risks are extremely low, even for thin walls such as the free wall of the right atrium.

This system also permits the safe attachment of a capsule of important size and/or weight, with a low impact on the tissue through the fastening stress distribution over several turns, along a generatrix of the capsule. Conversely, with the conventional solutions using anchoring methods extending the capsule at its distal end, the strain is much more concentrated, and further increased by the leverage effect on the screw due to the distance between the center of gravity of the capsule and its distal end. Another advantage of the disclosed invention is that the fixing mode is perfectly reversible. If necessary, it is possible to remove the capsule with minimal tissue damage, simply by a rotation exerted in the reverse direction than that of the helical anchoring screw.

Finally, note that the system of the invention is applicable to a fixation on the walls of many different natures, whether they are trabecular or smooth, with in all cases assurance of a robust attachment of the capsule to the wall.

Many variants of implementation are possible; the invention is of course not limited to the example described. Thus, it is possible to give the free interval e between an inside of the screw and the outside of the tubular body either a constant value or a variable value in the longitudinal direction of the capsule, if it is desired, by example, to limit the mechanical stress exerted on the tissue adjacent the pacing electrode. This variation of the interval may also be a variation viewed in a radial plane, the interval e then varying with the angular position of the helix point of the screw on a thread.

Furthermore, the pitch p of the helix of the anchoring screw 20 may also be either a constant value or a variable value, gradually proximally reduced to accentuate the phenomenon of tissue clamping.

The capsule can also be provided with segment radiopaque markers to help control under image intensifier the correct orientation of the capsule during implantation, with possibly a marker associated with the segment stimulation electrode 34, or formed by thereof.

The invention claimed is:

1. An intracardiac capsule, comprising:
   a cylindrical body having a distal end, a proximal end, and a contact region; and
   a helical anchoring screw surrounding at least a portion of a length of the cylindrical body, the helical anchoring screw including a free distal end and a proximal end coupled to the cylindrical body;
   wherein the contact region of the cylindrical body is disposed between the proximal end of the helical anchoring screw and the free distal end of the helical anchoring screw; and
   wherein a gap is formed between an inner diameter of the helical anchoring screw and an outer diameter of the cylindrical body in the contact region.

2. The intracardiac capsule of claim 1, wherein the gap between the inner diameter of the helical anchoring screw and the outer diameter of the cylindrical body in the contact region comprises a distance of 0.1 mm to 1 mm.

3. The intracardiac capsule of claim 2, wherein an anchoring screw outer diameter in the contact region is approximately 6 mm.

4. The intracardiac capsule of claim 1, further comprising an electrode disposed on the cylindrical body in the contact region.

5. The intracardiac capsule of claim 1, further comprising an electrode disposed on the helical anchoring screw.

6. The intracardiac capsule of claim 1, wherein the contact region comprises from twenty (20) percent to eighty (80) percent of a total length of the cylindrical body.

7. The intracardiac capsule of claim 1, wherein the gap is a constant value along throughout the contact region.

8. The intracardiac capsule of claim 1, wherein the gap along the contact region is a variable value.

9. The intracardiac capsule of claim 1, wherein a pitch of the helical anchoring screw is variable.

10. The intracardiac capsule of claim 1, wherein the free distal end of the helical anchoring screw surrounds the cylindrical body.

11. A method of implanting an intracardiac capsule having a cylindrical body and a helical anchoring screw, a proximal end of the helical anchoring screw affixed to the cylindrical body, the helical anchoring screw surrounding at least portion of a total length of the cylindrical body, the method comprising:
    positioning a distal end of the cylindrical body against a tissue wall to form an acute angle with the tissue wall such that a free distal end of the helical screw engages the tissue wall; and
    rotating the intracardiac capsule to cause progression of the helical screw in the tissue wall such that an axis of the cylindrical body is substantially parallel to the tissue wall after several rotations of the intracardiac capsule.

12. The method of claim 11, wherein only a portion of each turn of the helical anchoring screw that progresses in the tissue wall is embedded in the tissue wall.

13. The method of claim 11, wherein a gap is formed between an inner diameter of the helical anchoring screw and the outer diameter of the cylindrical body in a contact region of the cylindrical body.

14. The method of claim 13, wherein the gap comprises a distance of 0.1 mm to 1 mm.

15. The method of claim 13, wherein the cylindrical body includes a stop shoulder located at a proximal end of the contact region, wherein a stop shoulder diameter of the stop shoulder is approximately the same as the inner diameter of the helical anchoring screw.

16. The method of claim 13, wherein the contact region comprises from twenty (20) percent to eighty (80) percent of a total length of the cylindrical body.

17. An intracardiac capsule, comprising:
    a cylindrical body having a distal end, a proximal end, and a contact region, the contact region comprising from twenty (20) percent to eighty (80) percent of a total length of the cylindrical body; and
    a helical anchoring screw surrounding at least a portion of the total length of the cylindrical body including the contact region, the helical anchoring screw including a proximal end of the helical screw coupled to the cylindrical body and a free distal end of the helical anchoring screw;
    wherein the contact region of the cylindrical body is disposed between the proximal end of the helical anchoring screw and the free distal end; and
    wherein a gap is formed between an inner diameter of the helical anchoring screw and the outer diameter of the cylindrical body in the contact region.

18. The intracardiac capsule of claim 17, wherein the gap between the inner diameter of the helical anchoring screw and the outer diameter of the cylindrical body in the contact region comprises a distance of 0.1 to 1 mm.

19. The intracardiac capsule of claim 18, wherein the gap is a constant value along throughout the contact region.

20. The intracardiac capsule of claim 18, wherein the gap along the contact region is a variable value.

* * * * *